US 7,562,774 B2

(12) United States Patent
Uehata (10) Patent No.: US 7,562,774 B2
(45) Date of Patent: Jul. 21, 2009

(54) KIT HOLDING ADAPTER

(75) Inventor: Yoshiharu Uehata, Kyoto (JP)

(73) Assignee: Arkray, Inc., Kyoto (JP)

( * ) Notice: Subject to any disclaimer, the term of this patent is extended or adjusted under 35 U.S.C. 154(b) by 221 days.

(21) Appl. No.: 10/502,409

(22) PCT Filed: Feb. 6, 2003

(86) PCT No.: PCT/JP03/01276

§ 371 (c)(1),
(2), (4) Date: Jul. 23, 2004

(87) PCT Pub. No.: WO03/068071

PCT Pub. Date: Aug. 21, 2003

(65) Prior Publication Data

US 2005/0126938 A1    Jun. 16, 2005

(30) Foreign Application Priority Data

Feb. 15, 2002 (JP) .............................. 2002-037806
Apr. 25, 2002 (JP) .............................. 2002-123526

(51) Int. Cl.
*A61B 5/15* (2006.01)
*B65D 85/00* (2006.01)

(52) U.S. Cl. ....................... 206/305; 206/569; 206/363; 600/365

(58) Field of Classification Search ................. 206/305, 206/569, 570, 306, 572, 438, 363; 224/904, 224/912, 929, 930, 678, 681, 683, 666, 660, 224/679; 220/501; 600/347, 365; 422/104; 374/208
See application file for complete search history.

(56) References Cited

U.S. PATENT DOCUMENTS 3,917,456 A * 11/1975 Eckstein et al. ............... 422/85
4,008,614 A * 2/1977 Turner et al. ................ 374/158
4,446,970 A * 5/1984 Further ....................... 206/569
5,066,859 A * 11/1991 Karkar et al. ............. 250/339.09

(Continued)

FOREIGN PATENT DOCUMENTS

JP    8-233804    9/1996

(Continued)

*Primary Examiner*—Jila M Mohandesi
*Assistant Examiner*—Steven A. Reynolds
(74) *Attorney, Agent, or Firm*—Hamre, Schumann, Mueller & Larson, P.C.

(57) ABSTRACT

The present invention relates to a kit holding adapter (X1) for holding an analyzer (4) for analyzing a target analyte in a sample together with a sampling tool (5) used for taking a sample. The kit holding adapter (X1) includes a first holding portion (1) for holding the analyzer (4) and a second holding portion (2) for holding the sampling tool (5), for example. At least one of the first and second holding portions (1, 2) is preferably designed to expose a part of the analyzer (4) or the sampling tool (5) for performing the analysis of the sample with the analyzer (4) or for performing the sampling with the sampling tool (5) while the analyzer (4) or the sampling tool (5) are held by the adapter. The kit holding adapter (X1) may further include an article holding portion (3) for containing articles (45) used for at least one of the analyzer (4) and the sampling tool (5), or other articles used in conjunction with the analysis of the sample or the sampling.

20 Claims, 7 Drawing Sheets

U.S. PATENT DOCUMENTS

| | | | |
|---|---|---|---|
| 5,100,621 A * | 3/1992 | Berke et al. | 422/61 |
| 5,249,584 A * | 10/1993 | Karkar et al. | 600/578 |
| 5,251,800 A * | 10/1993 | Leenders | 224/678 |
| 6,068,119 A * | 5/2000 | Derr et al. | 206/305 |
| 6,142,298 A * | 11/2000 | Wu | 206/305 |
| 6,192,891 B1 * | 2/2001 | Gravel et al. | 604/187 |
| 6,360,888 B1 * | 3/2002 | McIvor et al. | 206/305 |
| 6,379,317 B1 * | 4/2002 | Kintzig et al. | 600/573 |
| 6,634,789 B2 * | 10/2003 | Babkes | 374/208 |
| D530,424 S * | 10/2006 | Manser et al. | D24/169 |
| D535,202 S * | 1/2007 | Sisk et al. | D10/57 |
| 7,252,804 B2 * | 8/2007 | Miyashita et al. | 422/104 |
| 2002/0013522 A1 * | 1/2002 | Lav et al. | 600/365 |
| 2002/0181545 A1 * | 12/2002 | Babkes | 374/208 |
| 2003/0002562 A1 * | 1/2003 | Yerlikaya et al. | 374/208 |
| 2003/0038047 A1 * | 2/2003 | Sleva et al. | 206/370 |

FOREIGN PATENT DOCUMENTS

| | | |
|---|---|---|
| JP | 2000-146961 | 5/2000 |
| JP | 2000-217804 | 8/2000 |
| JP | 3081309 | 11/2001 |
| JP | 2001-524680 | 12/2001 |
| WO | WO 98/19159 | 5/1998 |

* cited by examiner

KIT HOLDING ADAPTER

TECHNICAL FIELD

The present invention relates to a kit holding adapter for holding an analyzer for analyzing a target analyte together with a sampling tool for taking a sample.

BACKGROUND ART

Analyzers are used in various fields for analyzing a target analyte. For example, analyzers are used for measuring a target analyte in blood in the medical or sports field, or for analyzing ingredients in foods in the field of foods, and for determining the degree of pollution in water, soil or air in the environmental field.

For the above-described analysis, it is necessary to perform a sampling operation for collecting an enough amount of sample. For example, when an individual measures the glucose level in his or her blood, a sampling tool is used for collecting a sample (blood). A generally available sampling tool is a lancing device utilizing a lancet. The lancet of the lancing device punctures a finger or forearm for bleeding from the skin, whereby the blood is supplied to the analyzer for concentration measurement. In determining the glucose level in blood, use may be made of a personal blood sugar measuring device, for example, to which a measuring sensor may be fitted.

In self-measurement of the blood sugar, use needs to be made of a lancing device, a lancet, a personal blood sugar measuring device and a measuring sensor. Though these components are used as a set for measurement, blood sugar measurement is not always performed at home, so that the set owner must take the trouble of carrying all of the components needed for blood sugar measurement when he or she goes out. In addition, a risk of forgetting or losing part of the components will increase with an increasing number of components to be carried.

Recently, components for blood sugar measuring have been reduced in size for improving their portability. However, a diabetic also needs to carry insulin and an injector in addition to the components necessary for blood sugar measurement. Thus, the above-described problem is even more remarkable especially with respect to diabetics, and there is a greater need for improving the portability of blood sugar measuring components and the like.

As one solution to the above-described problem, JP-A-2001-524680 discloses a measuring device with a cutting implement. This measuring device includes a connector for removably attaching the cutting implement to the measuring device. The connector may be provided for example by forming a V-shaped dent on the measuring device for embracing engagement with the cutting tool, or by providing a clip on the cutting tool for engagement with a groove formed on the measuring device. In this way, the measuring device and the cutting tool, though two components, may be carried as one unit for improving their portability.

However, the measuring device with the cutting implement needs the connector to connect the measuring device and the cutting tool. Due to this structure, the connector can not be used for existing measuring devices or cutting implements (sampling tools), nor improve the portability of a specific measuring device and sampling tool which the user is currently using.

Further, if a large impact is applied to the measuring device with the cutting implement upon dropping, the connector may be damaged or deformed and therefore becomes no longer usable for connection to the cutting implement. For instance, in the case where the connector comprise a dent or clip, it is no longer possible to connect the cutting implement to the measuring device if the dent or clip is damaged or deformed.

DISCLOSURE OF THE INVENTION

An object of the present invention is to improve the portability of components (such as an analyzer or a sampling tool) needed for sample analysis on a long term basis.

According to the present invention, there is provided a kit holding adapter which is designed for holding an analyzer for analyzing a target analyte in a sample together with a sampling tool for taking sample.

The adapter may include a first holding portion for holding the analyzer and a second holding portion for holding the sampling tool.

The adapter according to the present invention may include a main body for holding the analyzer and the sampling tool, and an article holding portion for containing articles (e.g. analyzing sensors or lancets) used for at least one of the analyzer and the sampling tool, or other items (e.g. medication such as insulin, an injector, or a sterilizing tool) used in conjunction with the sample analysis or the sampling.

The main body preferably includes a first holding portion for holding the analyzer and a second holding portion for holding the sampling tool.

At least one of the first and second holding portions includes an opening for partly exposing the analyzer or the sampling tool for enabling at least either the analysis of the sample by the analyzer and the sampling by the sampling tool while the analyzer or the sampling tool is held by the adapter.

The first holding portion and the second holding portion may be separated by a partition wall which is formed with a cutout for connecting an inside of the first holding portion and an inside of the second holding portion.

The article housing portion preferably includes a plurality of containing rooms. The article housing portion may be removably attached to the body, so that the adapter can be reduced in size to provide improved portability when the article housing portion contains nothing. Alternatively, the article housing portion may be integrally formed with the body as one piece.

Each of the holding portions and containing rooms of the kit holding adapter according to the present invention may be colored differently. For example, the first holding portion may be colored red, the second holding portion may be colored yellow, a first containing room for housing non-used analyzing sensors may be colored green, a second containing room for housing non-used lancets may be colored purple, and a third containing room for housing used analyzing sensors and lancets may be colored black. In this way, the user can empirically and visually find out missing items at once, thereby facilitating timely supply of the missing items.

The adapter of the present invention can hold the analyzer and the sampling tool together and contain other items to compactly carry all components and items necessary for measurement. Thus, the burden on the user is reduced in carrying components needed for analysis such as blood sugar measurement.

This advantage may be obtained without making improvements or modifications to the analyzer and the sampling tool. Depending on the sizes of the particular analyzer and sampling tool which the user is currently using, a selection needs only to be made from a plurality of candidate adapters to best suit the particular combination of adapter and sampling tool, or an adapter is manufactured to suit the sizes of the components owned by the user. Analyzers, sampling tools, and other necessary components for analysis may vary in size from supplier to supplier. An adapter according to the present invention may be manufactured in a custom order manner to suit the particular combination of components owned by the user, using a mold selected from a plurality of candidate molds each prepared in advance to suit the size of each existing component.

An adapter according to the present invention is applicable to an analyzer and a sampling tool regardless of their model, type, year of manufacture, and supplier. Thus, the adapter of the present invention can be used to hold an existing analyzer and sampling tool together for carrying to improve their portability, so that there is no need for purchasing an integratable measuring kit.

Preferably, the adapter should at least have such a configuration as to stably hold the analyzer and the sampling tool while also facilitating subsequent removal of the thus held components. For example, each of the first and second holding portions includes an inner surface which is depressed and bulged to conform to the outer surface of each component. Due to this structure, the analyzer and the sampling tool are stably held by the kit holding adapter, so that they hardly play during transport or in use.

The adapter of the present invention may be provided with a spacer between the outer surface of the analyzer and the inner surface of the first holding portions as well as between the outer surface of the sampling tool and the inner surface of the second holding portion. In this way, the analyzer and the sampling tool are held stably in the first and second holding portions.

Each of the spacers may be formed separately from the main body or as a plurality of protrusions projecting from the inner surface of each holding portion.

A separate spacer may be selected from a plurality of spacers each prepared in advance to suit a different configuration. In this way, the adapter can stably hold the analyzer and the sampling tool regardless of the configuration of the analyzer and sampling tool. The separate spacer may be formed of an elastic material. Such a spacer is deformable to fit to the outer surface of the analyzer or the sampling tool, thereby stably holding the analyzer or the sampling tool.

On the other hand, in the case where a plurality of protrusions are provided to work as a spacer, unnecessary ones of the protrusions may be bent or removed for causing the remaining necessary protrusions to press the analyzer or the sampling tool, thereby stably holding these components. Preferably, the plurality of protrusions include plural kinds of protrusions having different heights.

The adapter is not limited in its outer configuration, but it should preferably be rounded as a whole. Such a configuration allows the user to comfortably grip the adapter while facilitating its insertion into a bag or pocket.

An adapter according to the present invention is typically made of plastic or metal. The adapter may also made of metal and provided with a thin plastic coating. Though the plastic coating provides an added thickness, it also provides abetter touch feel. Further, the adapter may be made of an elastic material such as rubber or silicone for serving the purpose of holding the analyzer, the sampling tool, and the other items as long as it substantially retains its shape.

However, since the adapter is desired to have a strength enough to avoid breakage due to dropping, it should be preferably made of a shock-resistant material. For avoiding any damage, peripheral portions of the adapter may be fitted with an elastic material for absorbing impacts. For better portability, the adapter is preferably made of a weight saving material.

Thus, the thickness of the adapter is selected in view of the demand for a weight reduction besides the requirements for withstanding external forces upon a fall. The thickness may be about 0.1 mm to 2.0 mm, depending on the material.

An analyzer held in an adapter according to the present invention is not limitative. For example, the adapter may be applicable to an analyzer of the type which requires mounting of an analyzing sensor, or of another type which does not require mounting of an analyzing sensor. An analyzing sensor is not limited to such a type that utilizes an oxygen reaction or an antigen-antibody reaction, but may be of the type which utilizes a chemical reaction. Further, a detection method in the analyzer is not limitative, so that the detection may be based on an optical method or an electrochemical method.

A sampling tool to be held in an adapter according to the present invention is not limitative. The sampling tool needs only to collect a sample necessary for analysis in the analyzer. Examples of sampling tools include a lancing device, a pipette or syringe used for reliably sampling a liquid.

BEST MODE FOR CARRYING OUT THE INVENTION

Preferred embodiments according to the present invention will be specifically described referring to the drawings, by taking as an example an adapter for holding a blood sugar measuring device (as an example of a measuring device) and a lancing device (as an example of a sampling tool).

A kit holding adapter X1 according to a first embodiment of the present invention is shown in FIGS. 1 to 5. The adapter X1 includes a first holding portion 1, a second holding portion 2, and an article housing portion 3.

Figure 1:
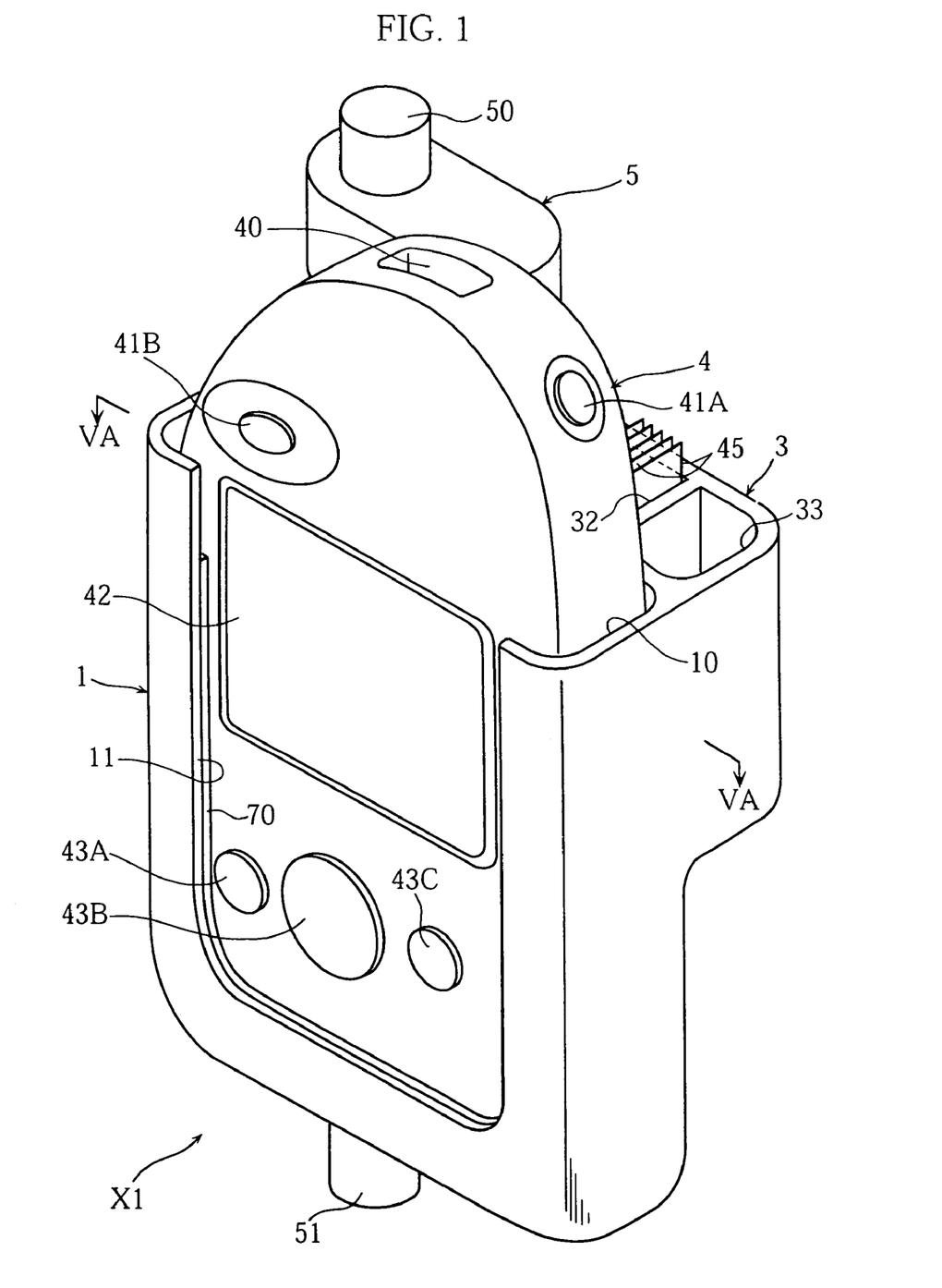
FIG. 1 is a front-side perspective view illustrating a kit holding adapter according to a first embodiment of the present invention in its state for holding a blood sugar measuring device and a lancing device.
Figure 2:
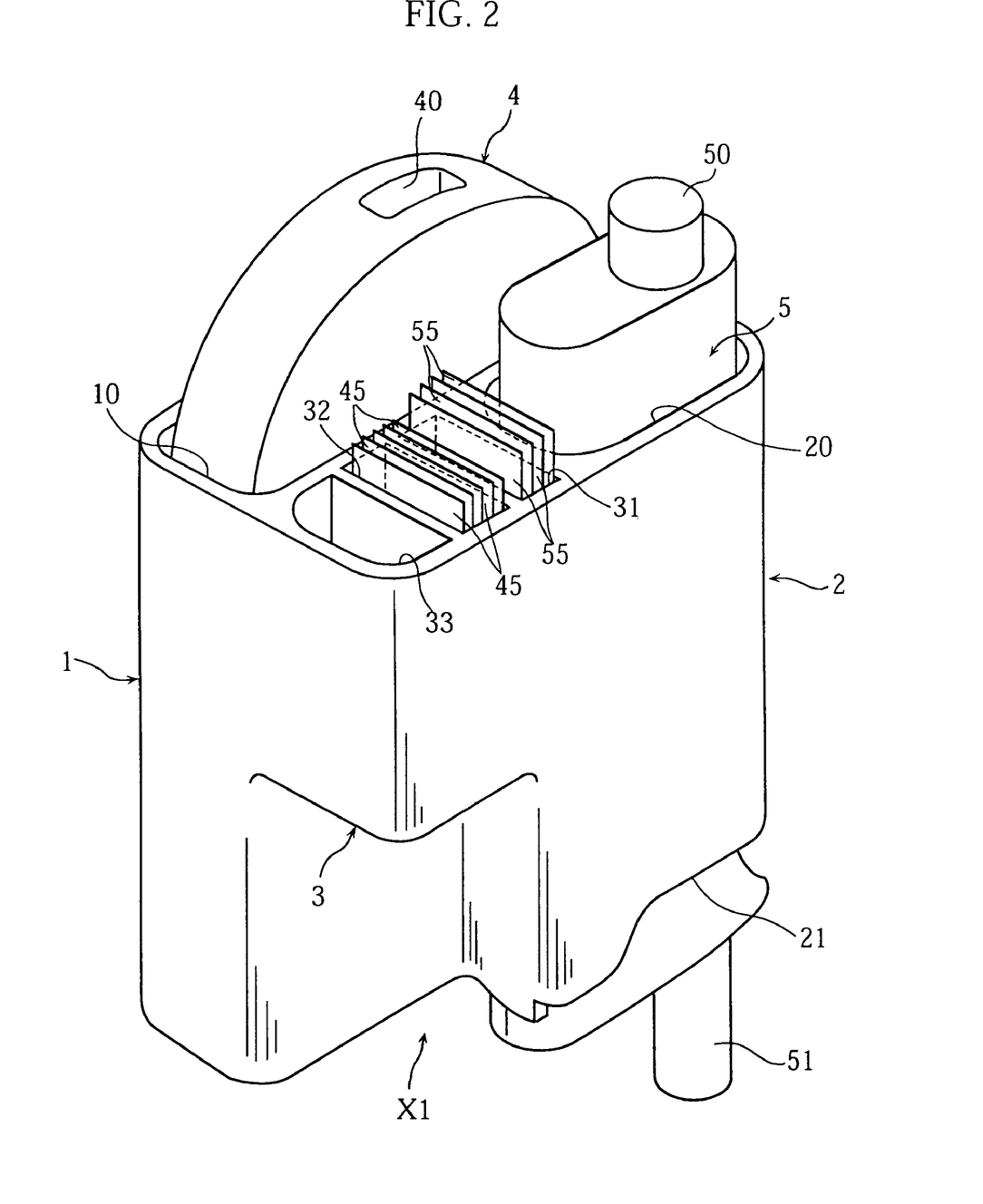
FIG. 2 is a rear-side perspective view illustrating the state of the adapter shown in FIG. 1.
Figure 3:
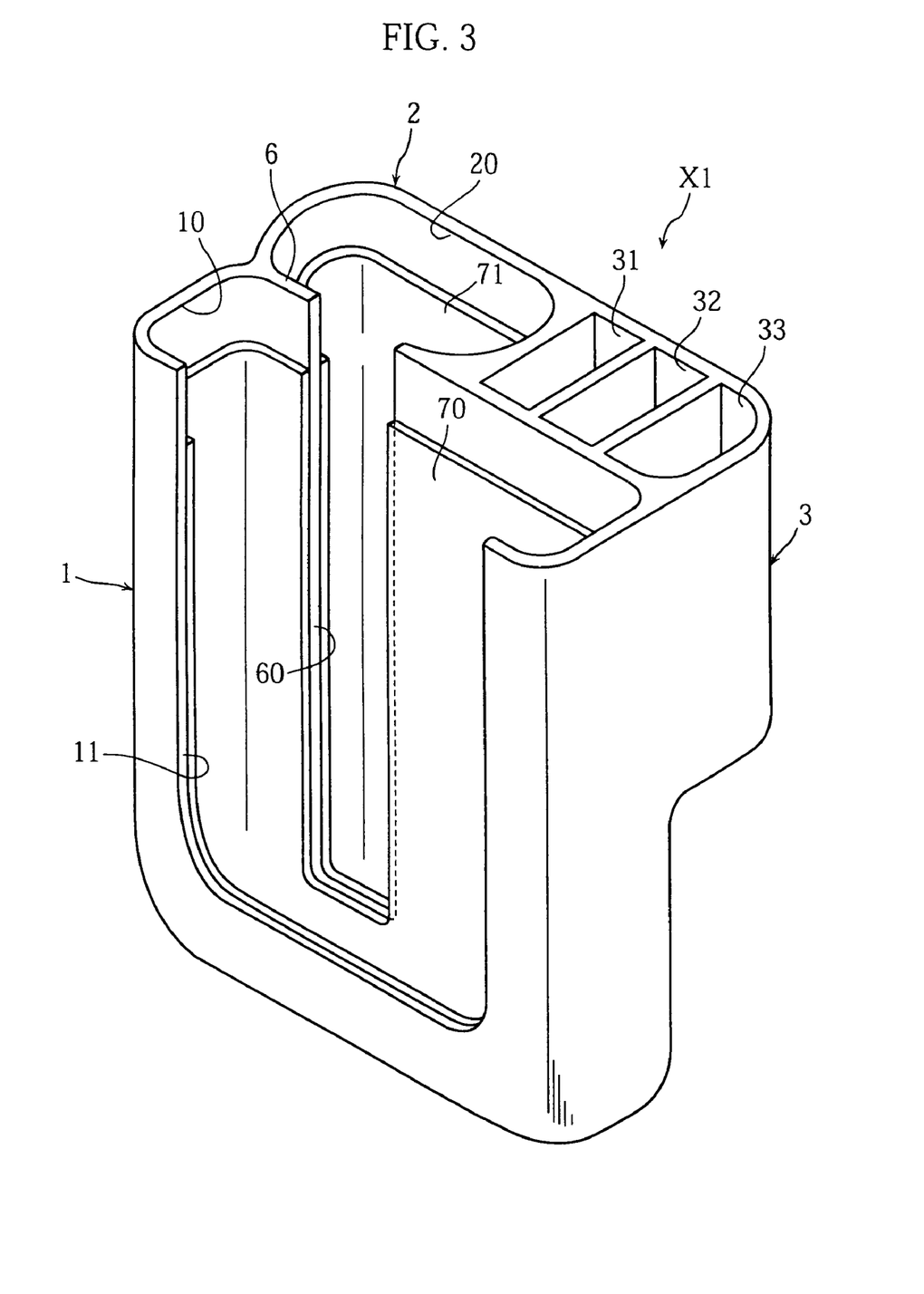
FIG. 3 is a front-side perspective view illustrating only the kit holding adapter shown in FIG. 1.
Figure 4:
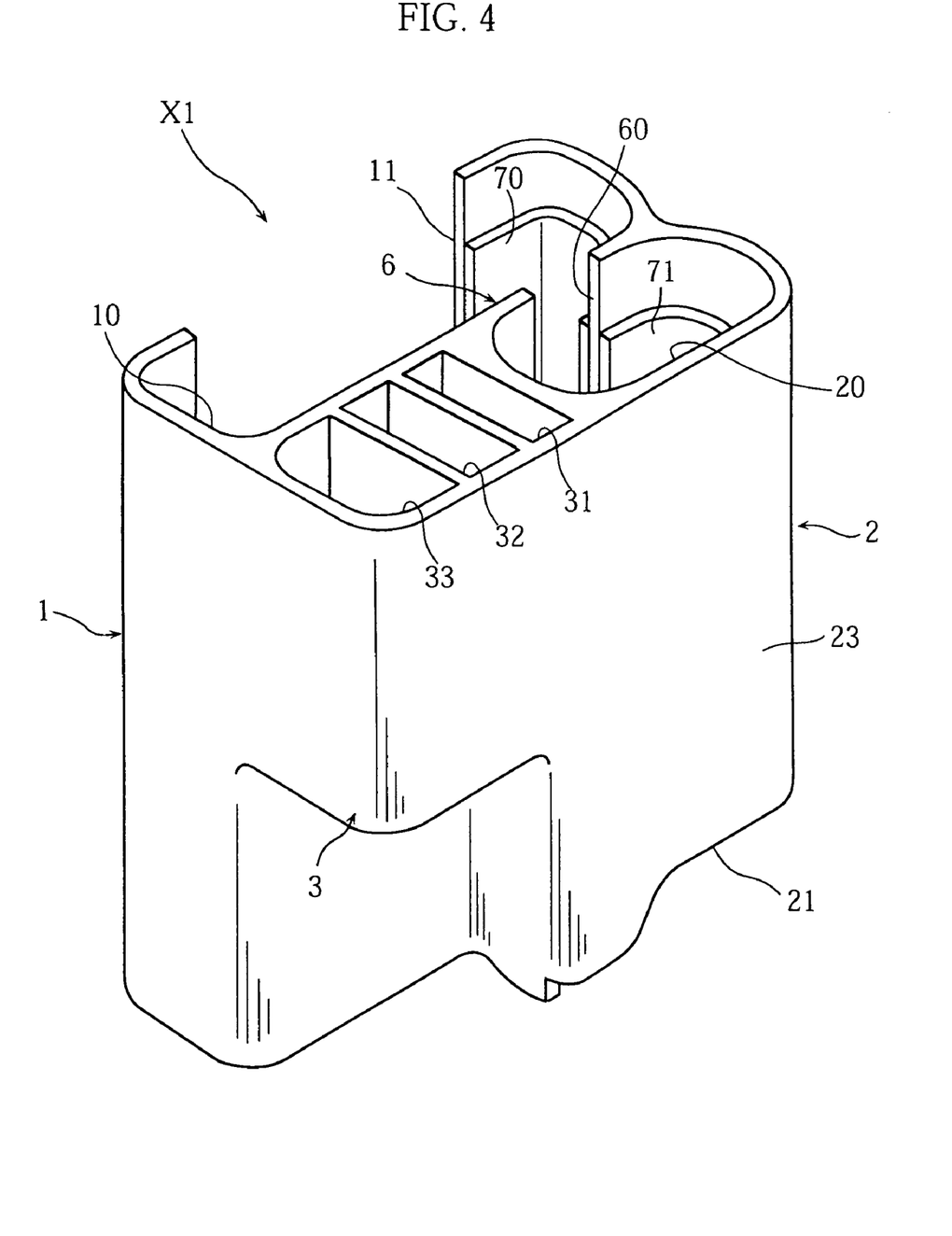
FIG. 4 is a rear-side perspective view illustrating only the kit holding adapter shown in FIG. 1.

As shown in FIGS. 1 and 2, the first holding portion 1 holds a blood sugar measuring device 4 for measuring the glucose level in blood. In use, the blood sugar measuring device 4 is fitted with a biosensor. As shown in FIGS. 3 and 4, the first holding portion 1 includes an upper opening 10 and a side opening 11 communicating with each other.

The upper and lower openings 20, 21 are designed to enable the lancing device 5 to be used for lancing when the lancing device 5 is held in the second holding portion 2. Specifically, as shown in FIG. 2, the upper opening 20 is designed to expose an operating portion of the lancing device 5 (e.g. an operating cap 50 for pushing out the lancet) when the lancing device 5 is held in the second holding portion 2.

The upper opening 20 is also designed as an insertion inlet for inserting the lancing device 5 into the second holding portion 2. On the other hand, the lower opening 21 is designed to expose a tip end 51 of the lancing device 5 for allowing removable attachment and movement of the lancet relative to the lancing device 5 when the lancing device 5 is held in the second holding portion 2. Due to this structure, the lancing device 5 can perform lancing while being held in the second holding portion 2 of the adapter X1.

As shown in FIGS. 1 and 2, the second holding portion 2 holds a lancing device 5 for sampling blood. The lancing device 5 is provided with a lancet for lancing the skin. As shown in FIGS. 3 and 4, the second holding portion 2 includes an upper opening 20 and a lower opening 21.

The upper and lower openings 20, 21 are designed to enable the lancing device 5 to be used for lancing when the lancing device 5 is held in the second holding portion 2. Specifically, as shown in FIG. 2, the upper opening 20 is designed to expose an operating portion of the lancing device 5 (e.g. an operating cap 50 for pushing out the lancet) when the lancing device 5 is held in the second holding portion 2. The upper opening 20 is also designed as an insertion inlet for inserting the lancing device 5 into the second holding portion 2. On the other hand, the lower opening 21 is designed to expose a tip end 51 of the lancing device 5 for allowing removable attachment and movement of the lancet relative to the lancing device 5 when the lancing device 5 is held in the second holding portion 2. Due to this structure, the blood sugar measuring device 4 can measure blood sugar while being held in the second holding portion 2 of the adapter X1.

As shown in FIGS. 3 and 4, the first and second holding portion 1, 2 are separated by a partition wall 6. The partition wall 6 is formed with a cutout 60 for conducting the inside of the first holding portion 1 with the inside of the second holding portion 2. The cutout 60 serves the purpose of lightening the adapter X1. However, the cutout 60 is dispensable in designing the adapter 1.

Figure 5:
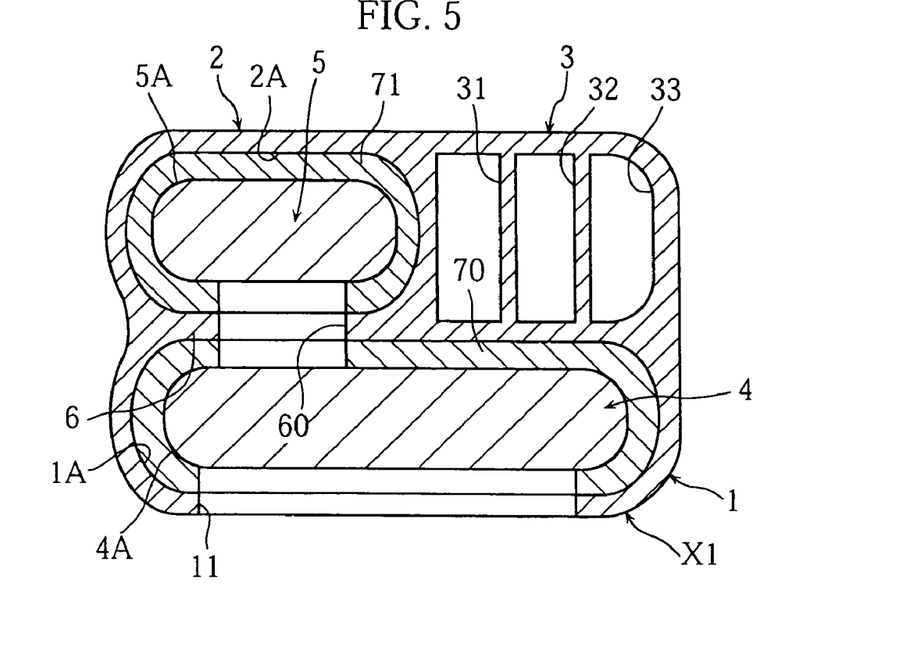
FIG. 5 is a sectional view taken along lines VA-VA in FIG. 1.

As shown in FIGS. 3 to 5, each of the first and the second holding portions 1, 2 is internally provided with spacers 70, 71. As shown in FIG. 5, the spacer 70 provides a spacing between the inner surface 1A of the first holding portion 1 and the outer surface 4A of the blood sugar measuring device 4. On the other hand, the spacer 71 provides a spacing between the inner surface 2A of the second holding portion 2 and the outer surface 5A of the lancing device 5. The spacers 70, 71 are formed by e.g. resin molding to be hardly deformable and externally conforms to the respective inner surfaces of the first and second holding portions 1, 2, while internally conforming to the respective outer surfaces of the blood sugar measuring device 4 and the lancing device 5. The spacers 70, 71 may be selected from a plurality of spacers each internally conforming to the outer surface of a different candidate blood sugar measuring device 4 or lancing device 5. In use, spacers are chosen to best suit the outer surface of the given blood sugar measuring device 4 and the given lancing device 5. In this way, the adapter can be widely applied to various types of existing blood sugar measuring device 4 and lancing device 5. In addition, the spacers 70, 71 can be used for stably holding the blood sugar measuring device 4 and the lancing device 5 in the first and second holding portions 1, 2 while facilitating insertion and removal of the blood sugar measuring device 4 and the lancing device 5. If the blood sugar measuring device 4 and the lancing device 5 are stably held, the blood sugar measuring device 4 and the lancing device 5 will hardly play during operation while the blood sugar measuring device 4 and the lancing device 5 are held in the first and the second holding portions 1, 2.

Figure 6:
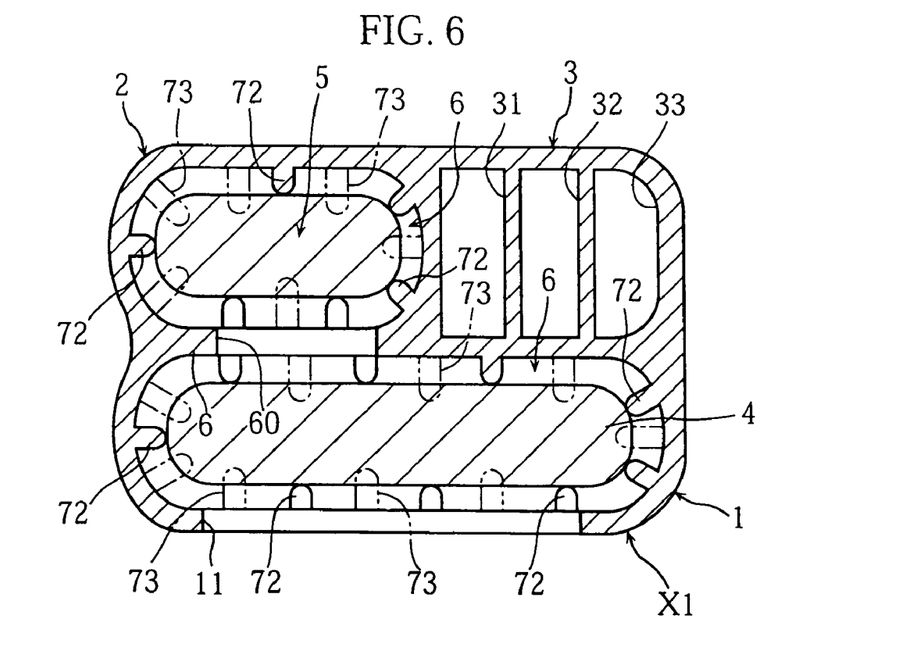
FIG. 6 is a sectional view similar to FIG. 5 but illustrating another example of spacers.

The spacers may be formed of an elastic material such as rubber or foam. Elastic spacers are advantageous in that they are deformable to conform to the outer surfaces of the blood sugar measuring device 4 and the lancing device 5, thereby obviating the need for preparing plural kinds of candidate spacers. Spacers may also be formed as shown in FIG. 6. The spacers shown in FIG. 6 comprise a plurality of protrusions 72, 73 projecting from the inner surfaces of the first and second holding portions 1, 2. The protrusions 72, 73 include protrusions 72 and protrusions 73 of different heights. For example, the higher protrusions 73 may be bent or removed as unnecessary for causing the protrusions 72, as needed, to contact the blood sugar measuring device 4 and the lancing device 5. In this way, the protrusions 72 press the blood sugar measuring device 4 and the lancing device 5 to stably hold the blood sugar measuring device 4 and the lancing device 5 in the first and second holding portions 1, 2.

As shown in FIG. 2, the article housing portion 3 is provided for containing articles used for the blood sugar measuring device 4 and the lancing device 5, and as shown in FIGS. 3 and 4, includes a first to third containing rooms 31, 32, 33.

As shown in FIG. 2, the containing rooms 31, 32 contain biosensors 45 used for the blood sugar measuring device 4 and lancets 55 used for the lancing device 5. In the figure, each of the biosensors 45 and the lancets 55 is packed in a laminated film. The containing room 33 contains used biosensors, used lancets, or the like. Each of the containing rooms 31, 32, 33 is upwardly, but may be provided with a lid for closing the upper opening to prevent the contained articles from falling out.

The kit holding adapter X1 holds the blood sugar measuring device 4 and the lancing device 5 together, thereby facilitating carriage by an user. The article housing portion 3 may contain e.g. biosensors 45 and lancets 55 used for the blood sugar measuring device 4 and the lancing device 5. Thus, the adapter X1 may be used to carry all items necessary for blood sugar measurement, thereby reducing the likelihood of leaving or losing necessary items for blood sugar measurement.

The kit holding adapter X1 can hold an existing blood sugar measuring device 4 and an existing lancing device 5 for improving the portability of the existing blood sugar measuring device 4 and lancing device 5. This advantage may be obtained without making improvements or modifications to the existing blood sugar measuring device 4 and lancing device 5, or without requiring. Further, there is no need for the user to newly purchase a measuring device integrated with a lancing device.

Next, a kit holding adapter X2 according to a second embodiment of the present invention will be described referring to FIGS. 7 and 8. In these figures, elements identical to those of the kit holding adapter X1 (refer to FIGS. 1 to 4) described already are given the same reference numbers, and duplicated description will be omitted.

Figure 7:
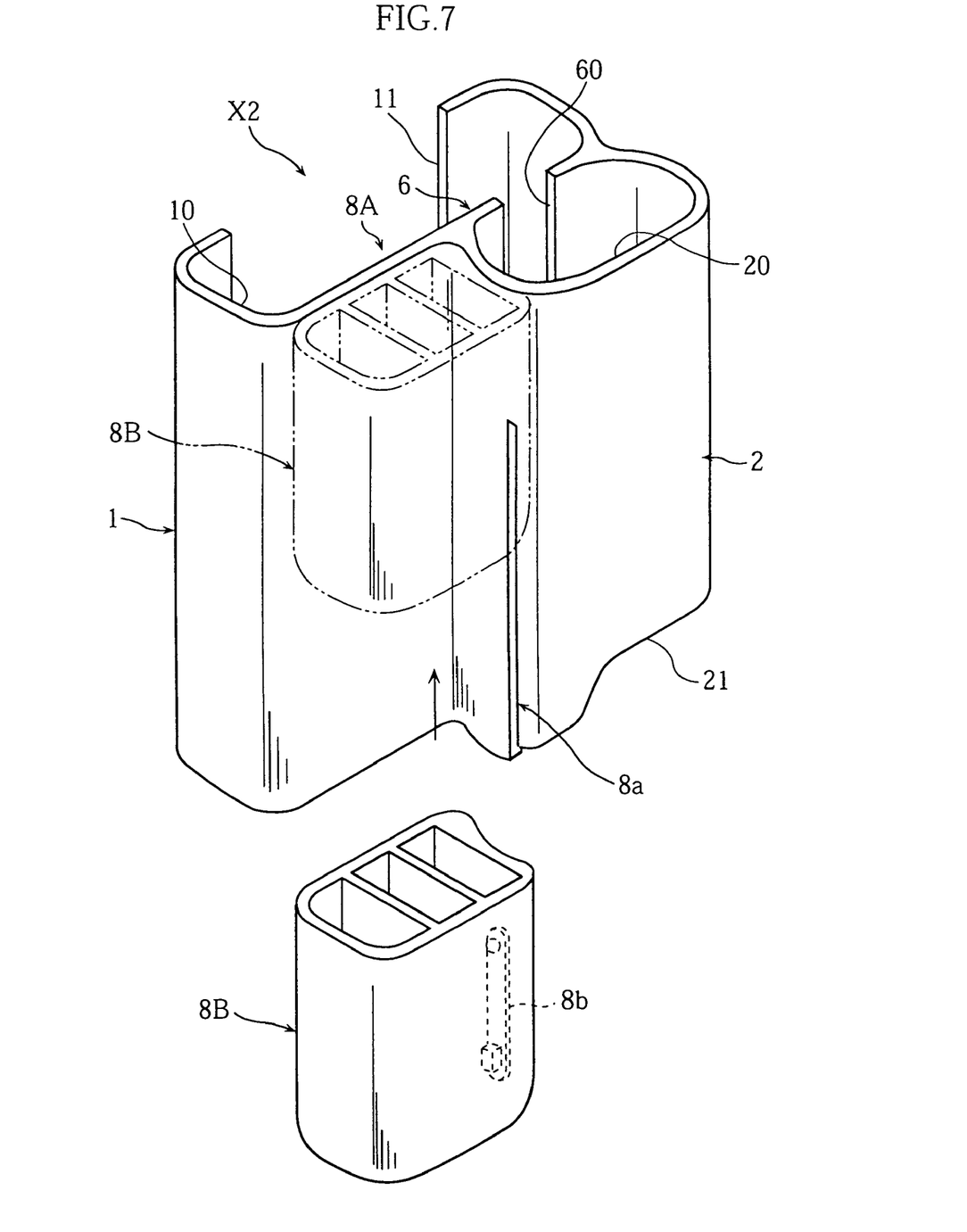
FIG. 7 is a rear-side perspective view illustrating a kit holding adapter according to a second embodiment of the present invention.
Figure 8:
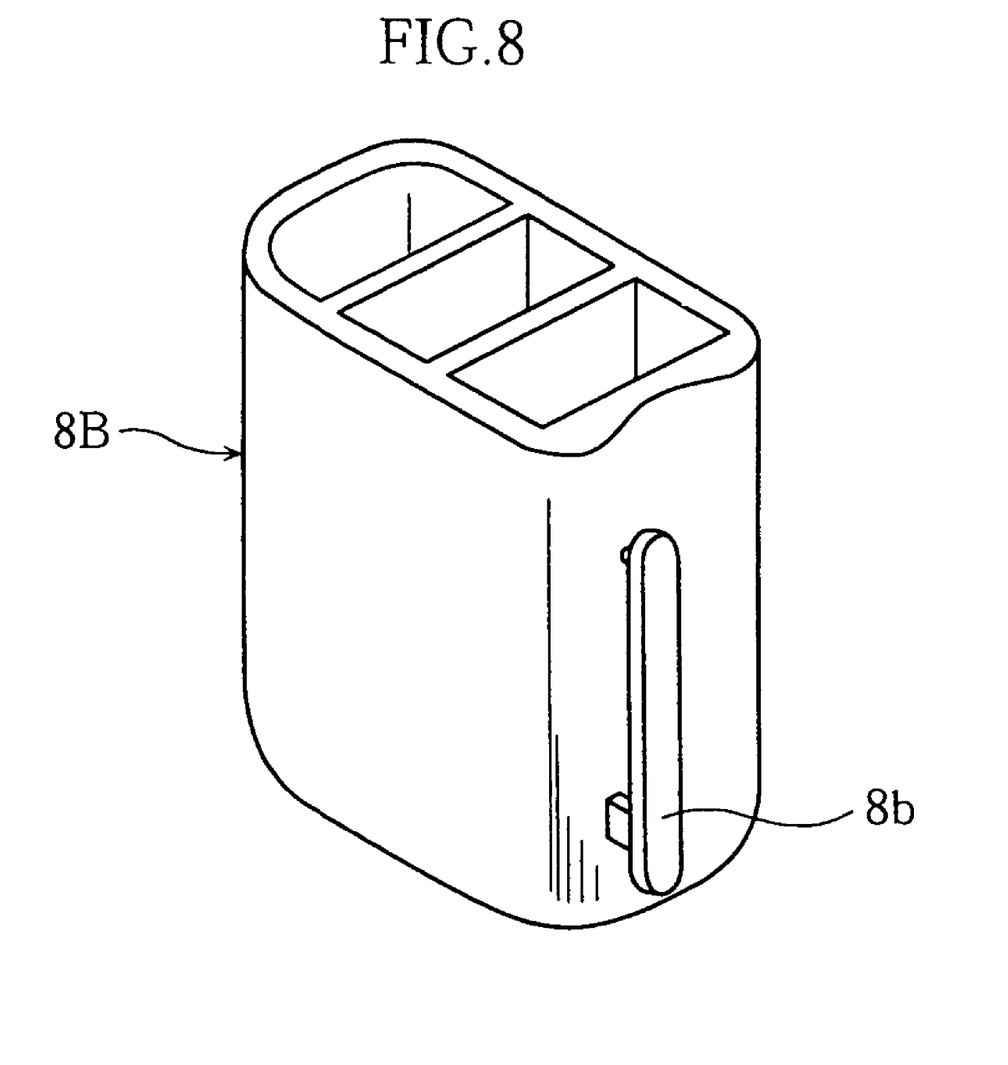
FIG. 8 is a perspective view illustrating an article housing portion of the adapter shown in FIG. 7.

As shown in FIG. 7, the adapter X2 includes a main body 8A formed with a first and a second holding portions 1, 2 while also including an article holder 8B removably attached to the main body. The main body 8A is formed with a vertically extending slit 8a, whereas the article holder 8B is provided with an engaging portion 8b, as shown in FIG. 8. Due to this structure, the article holder 8B can be attached to the main body 8A by engaging the engaging portion 8b of the article holder 8B with the slit 8a of the body 8A.

When the article holding portion 8B is not used, the main body 9A may be carried alone, thereby improving the portability and utility of the adapter X2.

An analyzer and a sampling tool to be held in the kit holding adapter are not limited to a blood sugar measuring device and a lancing device.

The number of the containing rooms in the article holding portion or holder is not limited to three but is variable. Further, the article holding portion or holder may be omitted.

The invention claimed is:

1. An analysis kit, comprising:
   an analyzer for analyzing a target analyte in a sample;
   a sampling tool for taking a sample, wherein the sampling tool includes an operating portion and a sampling tip; and
   an adapter housing for holding the analyzer and the sampling tool,
   wherein the adapter housing comprises:
      an upper end,
      a lower end,
      a first holding portion for holding the analyzer, and
      a second holding portion for holding the sampling tool,
         wherein the second holding portion includes an upper opening for exposing the operating portion of the sampling tool, and a lower opening for exposing the sampling tip of the sampling tool,
   wherein, when the second holding portion holds the sampling tool, the operating portion of the sampling tool projects out from the upper opening of the second holding portion beyond the upper end of the adapter housing, and the sampling tip of the sampling tool projects out from the lower opening of the second holding portion beyond the lower end of the adapter housings,
   wherein the analyzer comprises a blood sugar measuring device.

2. The analysis kit according to claim 1, wherein the first holding portion includes an upper opening for partly exposing the analyzer, and a side opening communicating with the upper opening of the first holding portion.

3. The analysis kit according to claim 1, wherein the first holding portion and the second holding portion are separated by a partition wall, the partition wall being formed with a cutout for communicating an inside of the first holding portion with an inside of the second holding portion.

4. The analysis kit according to claim 1, wherein the first and second holding portions are integrally formed as one piece.

5. The analysis kit according to claim 1,
   wherein the adapter housing further comprises an article holding portion for containing articles used for at least one of the analyzer and the sampling toot or other items used in conjunction with the sample analysis or the sampling.

6. The analysis kit according to claim 5, wherein the article holding portion includes a plurality of containing rooms.

7. The analysis kit according to claim 5, wherein the article holding portion is removably attached to the adapter housing.

8. The analysis kit according to claim 5, wherein the article holding portion is integrally formed with the adapter housing as one piece.

9. The analysis kit according to claim 1, further comprising a spacer for providing a spacing between an inner surface of the first holding portion and an outer surface of the analyzer, and/or between an inner surface of the second holding portion and an outer surface of the sampling tool.

10. The analysis kit according to claim 9, wherein the spacer comprises a plurality of protrusions projecting from at least one of the inner surfaces of the first and second holding portions.

11. The analysis kit according to claim 10, wherein the plurality of protrusions are bendable or removable when the analyzer or the sampling tool is inserted into the first holding portion or the second holding portion, respectively.

12. The analysis kit according to claim 11, wherein the plurality of protrusions include plural kinds of protrusions having different heights.

13. The analysis kit according to claim 9, wherein the spacer is formed of an elastic material.

14. The analysis kit according to claim 1, wherein the sampling tool comprises a lancing device used for piercing a lancing element into skin.

15. An analysis kit, comprising:
   an analyzer for analyzing a target analyte in a sample;
   a sampling tool for taking a sample, wherein the sampling tool includes an operating portion and a sampling tip; and
   an adapter housing for holding the analyzer and the sampling tool,
   wherein the adapter housing comprises:
      an upper end,
      a lower end,
      a first holding portion for holding the analyzer, and
      a second holding portion for holding the sampling tool,
         wherein the second holding portion includes an upper opening for exposing the operating portion of the sampling tool, and a lower opening for exposing the sampling tip of the sampling tool,
   wherein, when the second holding portion holds the sampling tool, the operating portion of the sampling tool projects out from the upper opening of the second holding portion beyond the upper end of the adapter housing, and the sampling tip of the sampling tool projects out from the lower opening of the second holding portion beyond the lower end of the adapter housing,
   wherein the adapter housing further comprises an article holding portion for containing articles used for at least one of the analyzer and the sampling tool, or other items used in conjunction with the sample analysis or the sampling, and
   wherein the article holding portion includes a plurality of containing rooms.

16. An analysis kit, comprising:
   an analyzer for analyzing a target analyte in a sample;
   a sampling tool for taking a sample, wherein the sampling tool includes an operating portion and a sampling tip; and
   an adapter housing for holding the analyzer and the sampling tool,
   wherein the adapter housing comprises:
      an upper end,
      a lower end,
      a first holding portion for holding the analyzer, and
      a second holding portion for holding the sampling tool,
         wherein the second holding portion includes an upper opening for exposing the operating portion of the sampling tool, and a lower opening for exposing the sampling tip of the sampling tool,
   wherein, when the second holding portion holds the sampling tool, the operating portion of the sampling tool projects out from the upper opening of the second holding portion beyond the upper end of the adapter housing, and the sampling tip of the sampling tool projects out from the lower opening of the second holding portion beyond the lower end of the adapter housing,
   wherein the adapter housing further comprises an article holding portion for containing articles used for at least one of the analyzer and the sampling tool, or other items used in conjunction with the sample analysis or the sampling, and wherein the article holding portion is removably attached to the adapter housing.

17. An analysis kit, comprising:

an analyzer for analyzing a target analyte in a sample;

a sampling tool for taking a sample, wherein the sampling tool includes an operating portion and a sampling tip; and an adapter housing for holding the analyzer and the sampling tool, wherein the adapter housing comprises:
 art upper end,
 a lower end,
 a first holding portion for holding the analyzer,
 a second holding portion for holding the sampling tool, wherein the second holding portion includes an upper opening for exposing the operating portion of the sampling tool, and a lower opening for exposing the sampling tip of the sampling tool, and
 a spacer for providing a spacing between an inner surface of the first holding portion and an outer surface of the analyzer, and/or between an inner surface of the second holding portion and an outer surface of the sampling tool, wherein, when the second holding portion holds the sampling tool, the operating portion of the sampling tool projects out from the upper opening of the second holding portion beyond the upper end of the adapter housing, and the sampling tip of the sampling tool projects out from the lower opening of the second holding portion beyond the lower end of the adapter housing, wherein the spacer comprises a plurality of protrusions projecting from at least one of the inner surfaces of the first and second holding portions.

18. The analysis kit according to claim 17, wherein the plurality of protrusions are bendable or removable when the analyzer or the sampling tool is inserted into the first holding portion or the second holding portion, respectively.

19. The analysis kit according to claim 18, wherein the plurality of protrusions include plural kinds of protrusions having different heights.

20. An analysis kit, comprising:

an analyzer for analyzing a target analyte in a sample;

a sampling tool for taking a sample, wherein the sampling tool includes en operating portion and a sampling tip; and an adapter housing for holding the analyzer and the sampling tool, wherein the adapter housing comprises:
 an upper end,
 a lower end,
 a first holding portion for holding the analyzer,
 a second holding portion for holding the sampling tool, wherein the second holding portion includes an upper opening for exposing the operating portion of the sampling tool, and a lower opening for exposing the sampling tip of the sampling tool, and
 a spacer for providing a spacing between an inner surface of the first holding portion and an outer surface of the analyzer, and/or between an inner surface of the second holding portion and an outer surface of the sampling tool, wherein, when the second holding portion holds the sampling tool, the operating portion of the sampling tool projects out from the upper opening of the second holding portion beyond the upper end of the adapter housing, and the sampling tip of the sampling tool projects out from the lower opening of the second holding portion beyond the lower end of the adapter housing, and wherein the spacer is formed of an elastic material.

* * * * *